United States Patent [19]

Tanigawa

[11] Patent Number: 5,232,884
[45] Date of Patent: Aug. 3, 1993

[54] PROCESS FOR PRODUCING A CARBONIC ACID ESTER

[75] Inventor: Hiroto Tanigawa, Hyogo, Japan

[73] Assignee: Daicel Chemical Industries, Ltd., Osaka, Japan

[21] Appl. No.: 906,473

[22] Filed: Jun. 30, 1992

[30] Foreign Application Priority Data

Jul. 1, 1991 [JP] Japan ................................ 3-256913

[51] Int. Cl.⁵ ............................................. C07C 69/96
[52] U.S. Cl. ...................................... 502/22; 558/277
[58] Field of Search ......................... 558/277; 502/22

[56] References Cited

U.S. PATENT DOCUMENTS 3,952,045  4/1976  Gaenzler et al. .................... 558/277

Primary Examiner—Mary C. Lee
Assistant Examiner—Joseph K. McKane
Attorney, Agent, or Firm—Sughrue, Mion, Zinn, Macpeak & Seas

[57] ABSTRACT

A process for producing a carbonic acid ester which comprises reacting an alcohol with carbon monoxide and oxygen in the presence of a catalyst comprising a compound of divalent copper is disclosed, wherein the catalyst deactivated as a result of the carbonic acid ester-producing reaction is regenerated by subjecting a reaction mixture or a concentrate thereof containing the deactivated catalyst to water-replacement treatment, followed by heat treatment and weak-acid treatment.

9 Claims, No Drawings

PROCESS FOR PRODUCING A CARBONIC ACID ESTER

FIELD OF THE INVENTION

The present invention relates to a process for producing a carbonic acid ester. More particularly, this invention relates to a carbonic acid ester-producing process which has enabled a catalyst to be industrially used repeatedly. The carbonic acid ester to be produced by the process of the present invention is an industrially important compound for use as an intermediate for polymers, medicines, and agricultural chemicals and as a solvent.

BACKGROUND OF THE INVENTION

In one conventional process for the industrial production of a carbonic acid ester, an alcohol has been reacted with phosgene. However, this process has problems, for example, that highly poisonous phosgene is used and that the reaction between an alcohol and phosgene yields highly corrosive hydrochloric acid as a by-product in a large quantity.

Therefore, a large number of processes have been proposed for the production of a carbonic acid ester without using phosgene. Among these is a commonly employed process in which an alcohol to be esterified is reacted with carbon monoxide and oxygen in the presence of a catalyst. Representative examples of the catalyst used in this process include a catalyst comprising a copper compound (JP-B-45-11129) and a catalyst comprising a combination of a palladium compound, a copper compound, and a base (JP-B-61-8816). (The term "JP-B" as used herein means an "examined Japanese patent publication".) Further, known as an improvement of the latter catalyst is one comprising a combination of a palladium compound, a weak acid salt or/and halide of copper, and a weak acid salt or/and halide of an alkali metal or alkaline earth metal (JP-A-1-287062). (The term "JP-A" as used herein means an "unexamined published Japanese patent application.)

The above-described catalysts, however, still have problems which should be overcome in order to utilize these catalysts in the industrial production of carbonic acid esters. Illustratively stated, in the case of using a copper compound as a catalyst, the copper compound, which has a low solubility, should be used in a large amount in order to obtain an effective reaction rate, since the catalytic activity of the copper compound is generally low. However, there are cases where the copper compound as a catalyst changes into copper hydroxychloride or other compounds according to the reaction conditions used and, as a result, the activity of the catalyst decreases.

In the case of the catalyst comprising a combination of a palladium compound, a copper compound, and a base, since water and oxalic acid are formed as by-products of the reaction and accumulate with the progress of the reaction, part of the catalytic components react with these by-products and separate out as an insoluble hydroxide, oxalate, or metal, resulting in a decrease in catalytic activity. It is, therefore, difficult to industrially use the catalyst continuously or repeatedly.

As apparent from the above, an industrially important theme for the conventional processes using either the catalyst comprising a copper compound or the catalyst based on the combination of a palladium compound and a copper compound is to establish a method of recovering or regenerating the catalyst.

SUMMARY OF THE INVENTION

The present inventors have made intensive studies in order to overcome the above-described problems and to enable carbonic acid ester production processes using the above-described catalysts to be utilized industrially. As a result, it has been found that catalyst regeneration can be attained by subjecting the reaction mixture containing insolubilized and deactivated catalytic components to water-replacement treatment, followed by heat treatment and treatment with a weak acid which, in the case where a salt of a weak acid has been used as a catalytic component, preferably is the same as the weak acid constituting part of the catalytic component. The present invention has been completed based on this finding.

Accordingly, the present invention provides a process for producing a carbonic acid ester which comprises reacting an alcohol with carbon monoxide and oxygen in the presence of a catalyst comprising a compound of divalent copper, wherein the catalyst deactivated as a result of the carbonic acid ester-producing reaction is regenerated by subjecting the reaction mixture or a concentrate thereof containing the deactivated catalyst to water-replacement treatment, followed by heat treatment and weak-acid treatment.

DETAILED DESCRIPTION OF THE INVENTION

Catalyst

The catalyst used in the process of the present invention for producing a carbonic acid ester contains a compound of divalent copper. Examples of the divalent copper compound include cupric salts of such weak acids as acetic acid, pivalic acid, benzoic acid, and other carboxylic acids, cupric hydrobromate, cupric carbonate, cupric salts of such weak acids as phenol, cresol, p-chlorophenol, and other phenols, and cupric halides such as cupric chloride and cupric bromide. Such a divalent copper salt is used in an amount of generally from 1 to 3,000 mmol, preferably from 10 to 1,000 mmol, per liter of the alcohol.

In combination with the divalent copper salt, a compound of either an alkali metal or an alkaline earth metal may be used as a catalytic component. Examples of the alkali metal or alkaline earth metal compound include chlorides, bromides, iodides, acetates, and other compounds of lithium, sodium, potassium, rubidium, cesium, beryllium, magnesium, calcium, and barium. Such an alkali metal or alkaline earth metal compound may preferably be used in an amount of from 1/10 to 10 mol per mol of the divalent copper salt. A more preferred range of the amount thereof is such that the atomic ratio of halogen to copper in the catalyst is from $\frac{1}{4}$ to 4.

A platinum group compound may further be used as a catalytic component. Examples thereof include halides, acetates, nitrates, and other compounds of ruthenium, rhodium, and palladium. Of these, palladium salts are particularly preferred. Although the amount of such a platinum group compound to be used is not particularly limited, it preferably is 1/10 mol or less per mol of the divalent copper salt from an economical standpoint.

Raw Materials

Examples of the alcohol to be used as a raw material for a carbonic acid ester in the present invention include saturated aliphatic alcohols such as methanol and ethanol, unsaturated aliphatic alcohols such as allyl alcohol, and aromatic alcohols such as phenols, and further include diols and polyols. Of these, alcohols having from 1 to 20 carbon atoms are preferred. The gaseous reactants, i.e., carbon monoxide and oxygen, each may be either a high-purity gas or a gas diluted with a gas inert in the reaction, such as nitrogen, argon, or carbon dioxide. Therefore, air may be used as an oxygen source.

Reaction Conditions

In the presence of the catalyst described above, the carbonic acid ester-producing reaction according to the present invention may be conducted by allowing the reactants to react at ordinary pressure or an increased pressure, preferably at from 1 to 100 atm. In the case where the gaseous reactants are used after being diluted with an inert gas, the partial pressure of carbon monoxide in the reaction system may be regulated in the range of from 0.1 to 30 atm and that of oxygen in the range of from 0.05 to 10 atm. The reaction temperature may be in the range of from 20° to 250° C.

Regeneration of Catalyst

The catalyst regeneration method in the present invention comprises the step of subjecting either the reaction mixture containing deactivated catalytic components that have been insolubilized and precipitated in various forms such as a metal oxalate, metal oxide, metal hydroxide, metal carbonate, elemental metal, etc. or a concentrate of the reaction mixture to water-replacement treatment, followed by the steps of heat treatment and weak-acid treatment. The weak acid used in the weak-acid treatment preferably is one which is the same as a constituent of one of the catalytic components if the catalytic component is a weak acid salt. Each of these steps is explained below.

After completion of the carbonic acid ester-producing reaction, the resulting reaction mixture containing a precipitated deactivated catalyst is first subjected to water-replacement treatment prior to heat treatment. The reasons for this are as follows: (1) the reducing substances and combustible matter present in the reaction mixture should be removed before the heat treatment because it is usually preferred to conduct the heat treatment in the presence of oxygen or air in an oxidizing atmosphere; and (2) the raw-material alcohol remaining unreacted and the carbonic acid ester produced will be lost in the heat treatment because they are decomposed under high-temperature conditions.

This water-replacement treatment is conducted until the concentration of the organic substances, such as methanol, carbonic acid ester, etc., in the reaction mixture becomes 5% or less, preferably 2% or less. Although the reaction mixture may be subjected as it is to the water-replacement treatment, a concentrate of the reaction mixture is usually subjected to the treatment, because use of a concentrate is advantageous in the amount of water to be used and in apparatus. The concentrate of the reaction mixture can be obtained by concentrating the reaction mixture by distilling away about 95% of a carbonic acid ester, water and an unreacted alcohol in the reaction mixture. The carbonic acid ester can be taken out when the reaction mixture is concentrated to the concentrate and the water-replacement is carried out.

After the water-replacement treatment, heat treatment is conducted. The heating temperature should be 100° C. or higher, but it is selected in the range of generally from 150° to 1,000° C. from the standpoint of treating rate and apparatus. For example, the heat treatment can be carried out at from 170° to 190° C. for from 2 to 4 hours. It should be noted that if the heat treatment is performed in an oxygen-free atmosphere, metallic ingredients in the catalyst, especially copper, are apt to be disadvantageously reduced into the monovalent state or elemental metal state, while if the heat treatment is performed in a reducing atmosphere, it is very difficult to decompose metal oxalates. Because of this, it is usually preferable to carry out the heat treatment in the presence of oxygen or air.

The catalyst which has undergone the heat treatment is then treated with a weak acid, preferably with the same weak acid as that constituting part of a weak acid salt as one of the catalytic components. As the weak acid, use may be made of one whose copper salt dissolves in the raw-material alcohol or reaction mixture in a catalytic amount. For example, in the case where the alcohol is methanol or the like, a lower aliphatic carboxylic acid is advantageously used.

The amount of the weak acid used for the weak-acid treatment is usually 1.5 mol or more, preferably in the range of from 2 to 5 mol, per mol of the copper contained in the catalyst present in the mixture being treated. Although this treatment may be given to the heat-treated mixture as it is, the efficiency of the weak-acid treatment becomes higher as the concentration of the weak acid in the mixture being treated increases higher. For example, in the case of using acetic acid as a weak acid in an amount of 2 mol per mol of copper, the recovery of copper (the percentage of soluble copper after the treatment to the total amount of copper) was 46% when the mixture being treated had an acetic acid concentration of 3%, whereas the recoveries of copper were 53%, 69%, and 95% at acetic acid concentrations of 32%, 45%, and 75%, respectively.

Although the weak-acid treatment may be performed at room temperature, it is preferred to conduct the treatment at an elevated temperature in order to accelerate the treatment. For example, when acetic acid is used as a weak-acid, the weak-acid treatment is carried out preferably at a temperature of from 100° to 115° C. If a weak acid was added in an amount larger than the required amount, the excess weak acid may by removed after the treatment by evaporation. After completion of the weak-acid treatment, an alcohol to be a raw material in the subsequent carbonic acid ester synthesis or a solvent for the reaction is added to the weak acid-treated mixture, thereby to dissolve the soluble matter into the alcohol or solvent (this solution being referred to as solution A) and separate it from the insoluble matter. The insoluble matter can be reused after being treated by an adequate method.

In addition, since the insoluble matter resulting from the regeneration treatments described above does not contain any expensive platinum group compound, e.g., palladium, the insoluble matter can be discarded without any fear of posing a cost problem. That is, platinum group compounds are soluble in the reaction mixture or a concentrate thereof in the present invention since the reaction mixture or a concentrate thereof contains much larger amount of cupric ions ($Cu^{2+}$) than platinum group compounds. On the other hand, solution A containing the regenerated catalyst can be used after fresh catalytic components corresponding to the discarded insoluble matter are added thereto.

According to the present invention, a catalyst containing a deactivated divalent copper compound can be regenerated efficiently and, hence, repeated industrial use of the catalyst has become possible.

The present invention will be explained below in more detail with reference to the following Example and Comparative Example, but the invention is not construed as being limited thereto. Although the process of Example was conducted batchwise, it is a matter of course that either of the synthesis reaction and catalyst regeneration in the process can also be carried out continuously.

EXAMPLE 1

Into a glass-lined reactor having a capacity of 5 liters was introduced 3 liters of methanol containing, as a catalyst, 0.34 mmol/l of palladium chloride, 57 mmol/l of copper acetate, and 57 mmol/l of magnesium chloride dissolved therein. While CO and $O_2$ were kept being fed to the reactor at rates of 200 Nl/h and 100 Nl/h, respectively, the methanol was reacted with the gaseous reactants at a total pressure of 21.1 atm and a temperature of 135° C. After the reaction was conducted for 3 hours, the reaction mixture was cooled and then analyzed by gas chromatography. As a result, it was found that dimethyl carbonate (hereinafter abbreviated as DMC) had been formed in a yield of 20.1% based on the methanol. Further, analysis of the reaction mixture by atomic absorption spectroscopy revealed that 99%, 24%, and 34% of the Pd, Cu, and Mg, respectively, introduced in the reactor had been insolubilized and precipitated.

1,000 Grams of the reaction mixture (including the precipitate) was concentrated with a rotary evaporator and then with an evaporating vessel, thereby giving 50 g of a concentrate. Subsequently, 5 g of water was added thereto and the resulting mixture was concentrated to remove 5 g of volatile matter by evaporation. This procedure was repeated until the supernatant came to have a water content as determined by gas chromatography of 98% or more, thereby carrying out water-replacement treatment. The resulting liquid mixture was placed in a glass-lined autoclave having a capacity of 5 liters, and then heat-treated therein at 190° C. for 2 hours while air was kept being fed at a rate of 200 Nl/h at a total pressure of 20 atm. After cooling and pressure release, the contents were analyzed by liquid chromatography. As a result, it was found that 98% of the metal oxalates had been decomposed.

The heat-treated mixture was then concentrated with an evaporating vessel to give 25 g of a concentrate. Subsequently, 5.9 g of acetic acid was added to the concentrate and the resulting mixture was stirred at 60° C. for 1 hour. To the reaction mixture was added methanol in such an amount as to result in a total amount thereof of 1,000 g. This mixture was stirred at 20° C. for 1 hour and the insoluble matter was then separated out by vacuum filtration. The thus-obtained filtrate and cake were analyzed by atomic absorption spectroscopy. As a result, it was found that the filtrate contained, dissolved therein, 100%, 96%, and 97% of the Pd, Cu, and Mg, respectively, which had been introduced in the reactor for the DMC-producing reaction, while the cake contained 0%, 4%, and 3% of the introduced Pd, Cu, and Mg, respectively.

To the filtrate obtained above were added 0.5 g of copper acetate and 0.3 g of magnesium acetate. (This liquid is referred to as "regenerated catalyst-containing raw-material liquid B".) The concentrations of palladium, copper, magnesium, chlorine ion, and acetic acid ion dissolved in raw-material liquid B were determined by atomic absorption spectroscopy, titrimetric analysis, and liquid chromatography. As a result, all of the determined values of these concentrations were substantially the same as those for the raw-material liquid containing a fresh catalyst before being used in the DMC-producing reaction described above, that is, the differences between the determined concentration values for raw-material liquid B and those for the raw-material liquid containing a fresh catalyst were within the determination errors.

Using regenerated catalyst-containing raw-material liquid B, DMC synthesis was conducted in the same manner as in the above-described first synthesis employing a fresh catalyst. As a result, DMC was obtained in a yield of 20.2%, demonstrating that the regenerated catalyst had an activity equal to that of the fresh catalyst.

COMPARATIVE EXAMPLE 1

(DMC Synthesis without Catalyst Regeneration)

Using a fresh catalyst, DMC-producing reaction was conducted in the same manner as in Example 1, thereby obtaining DMC in a yield of 21.3%. 1,000 Grams of the resulting reaction mixture was concentrated with a rotary evaporator to give 25 g of a concentrate. Methanol was added to the concentrate in such an amount as to result in a total amount thereof of 1 liter. DMC synthesis was then conducted using the resulting mixture in the same manner as in the above-described first synthesis employing a fresh catalyst. As a result, the yield of DMC was 0.86%.

While the invention has been described in detail and with reference to specific embodiments thereof, it will be apparent to one skilled in the art that various changes and modifications can be made therein without departing from the spirit and scope thereof.

What is claimed is:

1. A process for producing a carbonic acid ester, which comprises the following steps:
   (a) reacting an alcohol with carbon monoxide and oxygen in the presence of a catalyst comprising a compound of divalent copper to produce a reaction mixture comprising the carbonic acid ester, unreacted organic matter, and a deactivated catalyst;
   (b) regenerating said deactivated catalyst in said reaction mixture by:
      (i) removing said ester and said organic matter from the reaction mixture and replacing with water until the concentration of water in the reaction mixture is greater than 95%;
      (ii) heating the reaction mixture from step (i) to a temperature of 150° to 1000° C.;
      (iii) adding 1.5 moles or more per mol of copper in said catalyst of a weak acid to the reaction mixture from step (ii); and
   (c) recovering said catalyst.

2. A process for producing a carbonic acid ester as claimed in claim 1, wherein step (b)(ii) is performed in the presence of oxygen.

3. A process for producing a carbonic acid ester as claimed in claim 1, wherein the concentration of water in the reaction mixture in step (b)(i) is greater than 98%.

4. A process for producing a carbonic acid ester as claimed in claim 1, wherein said step (b)(iii) is carried out at a temperature of 100°–115° C.

5. A process as claimed in claim 1, wherein the catalyst comprises a mixture of a compound of divalent copper and a compound of either an alkali metal or an alkaline earth metal.

6. A process as claimed in claim 1, wherein the catalyst comprises a mixture of a compound of divalent copper, a compound of either an alkali metal or an alkaline earth metal, and a platinum group compound.

7. A process as claimed in claim 1, wherein the catalyst comprises a cupric salt of a weak acid and the weak-acid treatment is carried out using as a weak acid one which is the same as a constituent of the cupric salt of a weak acid.

8. A process as claimed in claim 1, wherein the weak-acid treatment is carried out at an elevated temperature.

9. A process for producing a carbonic acid ester, which comprises the following steps:
  (a) reacting an alcohol with carbon monoxide and oxygen in the presence of a catalyst comprising a compound of divalent copper to produce a reaction mixture comprising the carbonic acid ester, unreacted organic matter, and a deactivated catalyst;
  (b) regenerating said deactivated catalyst in said reaction mixture by:
    (i) distilling said reaction mixture to remove at least 95% of said ester and said organic matter therein;
    (ii) adding water to the reaction mixture from step (i) until the concentration of water in the reaction mixture is greater than 95%;
    (iii) heating the reaction mixture from step (ii) to a temperature of 150° to 1000° C.;
    (iv) adding 1.5 moles or more per mol of copper in said catalyst of a weak acid to the reaction mixture from step (iii); and
  (c) recovering said catalyst.

* * * * *